United States Patent
Chen et al.

(10) Patent No.: US 6,745,631 B2
(45) Date of Patent: Jun. 8, 2004

(54) METHOD OF MEASURING PORE DEPTH ON THE SURFACE OF A POLISHING PAD

(75) Inventors: Chih-Kun Chen, Taoyuan Hsien (TW); Chung-Min Lin, Taipei (TW)

(73) Assignee: Nanya Technology Corporation, Taoyuan (TW)

( * ) Notice: Subject to any disclaimer, the term of this patent is extended or adjusted under 35 U.S.C. 154(b) by 0 days.

(21) Appl. No.: 10/435,440

(22) Filed: May 9, 2003

(65) Prior Publication Data

US 2004/0020295 A1 Feb. 5, 2004

(30) Foreign Application Priority Data

Aug. 1, 2002 (TW) ........................................ 91117354 A

(51) Int. Cl.$^7$ .............................................. G01N 29/18
(52) U.S. Cl. .......................................... 73/597; 438/14
(58) Field of Search .......................... 73/597, 598, 620, 73/625; 438/14

(56) References Cited

U.S. PATENT DOCUMENTS

| | | | | |
|---|---|---|---|---|
| 4,953,147 A | * | 8/1990 | Cobb | 73/598 |
| 5,399,234 A | * | 3/1995 | Yu et al. | 438/14 |
| 6,269,700 B1 | * | 8/2001 | Nikolovski | 73/597 |

\* cited by examiner

*Primary Examiner*—John E. Chapman
(74) *Attorney, Agent, or Firm*—Quintero Law Office

(57) ABSTRACT

A method of measuring pore depth on the surface of a polishing pad during processing. In the present invention, a planar ultrasound sensing device is disposed a predetermined distance above the surface of a polishing pad. The planar ultrasound sensing device sends out a plurality of ultrasound signals to the surface and the pores therein, and receives a plurality of reflected signals from the pad surface and constituent pores. The difference between pore depth and the surface is determined to establish first depth difference data according to the time delay in the reflected signals. The polishing pad is rotated to obtain second to Nth depth difference data. A relational image relative to the surface and the pores of the polishing pad is obtained according to the first to Nth depth difference data.

6 Claims, 3 Drawing Sheets

METHOD OF MEASURING PORE DEPTH ON THE SURFACE OF A POLISHING PAD

BACKGROUND OF THE INVENTION

1. Field of the Invention

The present invention relates to a measuring method, and in particular to a method of measuring pore depth on the surface of a polishing pad during processing.

2. Description of the Related Art

During the manufacture of integrated circuits it is necessary to polish a thin wafer of semiconductor material to remove material and dirt from the surface thereof. Typically, a wet chemical abrasive or slurry is applied to a motor driven polishing pad while a semiconductor wafer is pressed against it in a process well known as chemical mechanical polishing (CMP). The polishing effects on the wafer result from both the chemical and mechanical actions.

The polishing pad contacts the wafer surface while both wafer and pad are rotating on different axes. The rotation facilitates the transport of the abrasive-containing polishing slurry between the pad and the wafer. The condition of the polishing pad directly affects the polishing rate of material removal and uniformity of the removal from the semiconductor wafer. Pad conditioning may take place during or after the polishing process. The most common method of pad conditioning is a mechanical abrasion of the pad surface. Materials such as steel blades or abrasive wheels are often used. While conditioning of the pad surface improves polishing uniformity and rates, it has the detrimental effect of removing a quantity of pad material. However, the polishing removal rate is still diminished, since the pores on the surface of the polishing pad retain particles within the slurry. Therefore, the polishing removal uniformity is degraded.

Presently, the only means available to measure pad condition is destructive to the polishing pad, such as cutting a piece from the pad and using a micrometer to measure surface depth. Thus, pad destruction may result and downtime is increased.

SUMMARY OF THE INVENTION

Accordingly, an object of the present invention is to measure pore depth and size on the surface of a polishing pad during processing without pad destruction.

According to the above mentioned objects, the present invention provides a method of measuring pore depth and size on the surface of a polishing pad during processing.

In the method of the present invention, a planar ultrasound sensing device is disposed a predetermined distance above the surface of a polishing pad. The planar ultrasound sensing device sends out a plurality of ultrasound signals to the surface and the pores therein, and receives a plurality of reflected signals from the pad surface and constituent pores. The difference between pore depth and the surface is determined to establish first depth difference data according to the time delay in the reflected signals. The polishing pad is then rotated to obtain second to Nth depth difference data. A relational image relative to the surface and the pores of the polishing pad is obtained according to the first to Nth depth difference data.

Also, the present invention displays the relational image relative to the surface and the pores of the polishing pad.

Also, the present invention computes a relationship between size and depth of the pores on the polishing pad according to the first to Nth depth difference data.

Also, the present invention calculates the pore size per unit surface area of the polishing pad according to the pore size and surface area of the polishing pad.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
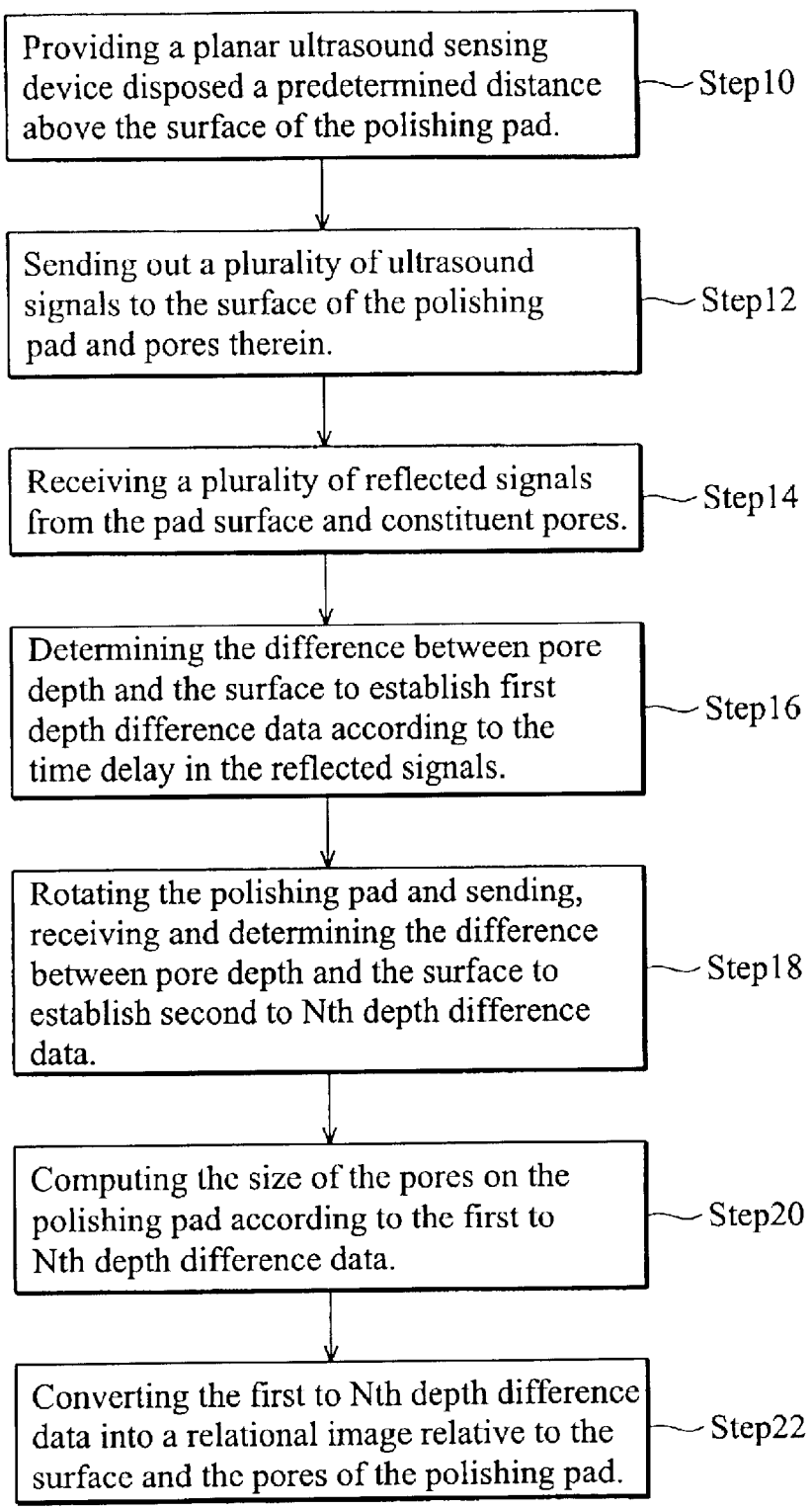
FIG. 1 is a flowchart of the measuring method according to the present invention.
Figure 2:
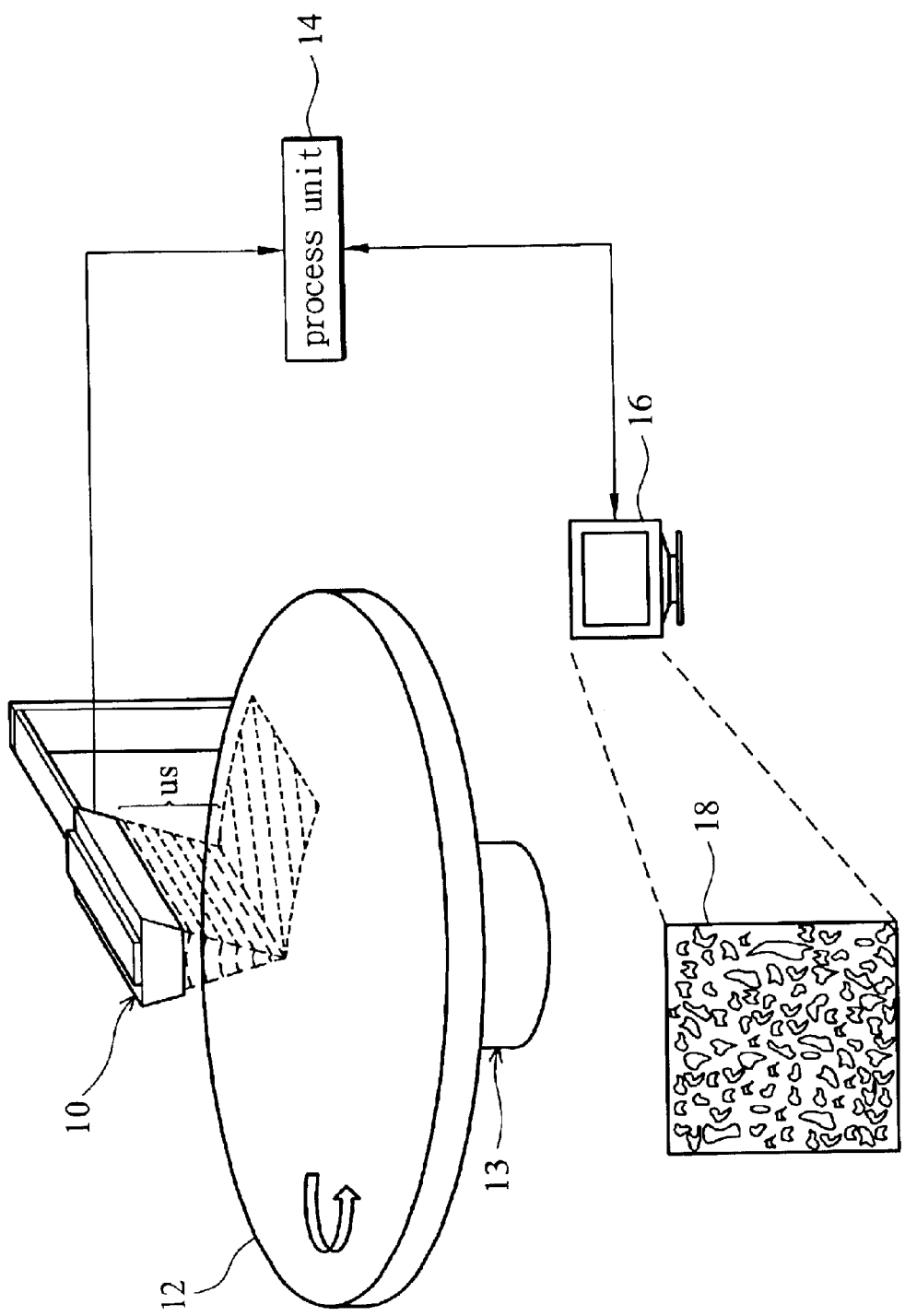
FIG. 2 is a diagram of the measuring method according to the present invention.

FIG. 1 is a flowchart of the measuring method according to the present invention. FIG. 2 is a diagram of the measuring method according to the present invention.

In step 10, a planar ultrasound sensing device 10 is disposed a predetermined distance above the surface of the polishing pad 12, wherein the polishing pad 12 is disposed on a rotating platen 13 of a polishing machine. For example, the planar ultrasound sensing device 10 can include a plurality of ultrasound transmitters and corresponding ultrasound receivers, wherein the operational frequency of the ultrasound transmitters is 0.1 to 5 GHz. Typically, the ultrasound transmitters transmit ultrasound signals us to a target and the corresponding ultrasound receivers receive the reflected signals from the target.

Figure 3A:
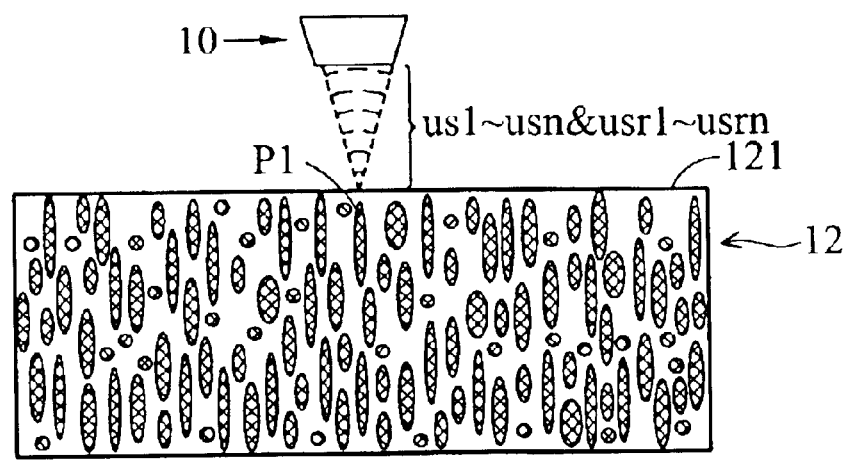
FIG. 3a is another diagram of the measuring method according to the present invention.

In step 12, the planar ultrasound sensing device 10 sends out a plurality of ultrasound signals us1~usn to the surface 121 of the polishing pad 12 and pores p1 thereon, as shown in FIG. 3a. FIG. 3a is another diagram of the measuring method according to the present invention.

In step 14, planar ultrasound sensing device 10 receives the reflected signals usr1~usrn from the surface 121 and the depth of the pores p1 on the polishing pad 12.

A process unit 14 is coupled to planar ultrasound sensing device 10 shown in FIG. 2. For example, the process unit 14 is a computing device or a computer. In step 16, the process unit 14 determines the difference between pore p1 depth and the surface 121 and establishes first depth difference data according to the time delay in the reflected signals. Usually, the pore depth on the surface of the polishing pad is in tens and hundreds of micrometers ($\mu$m).

Figure 3B:
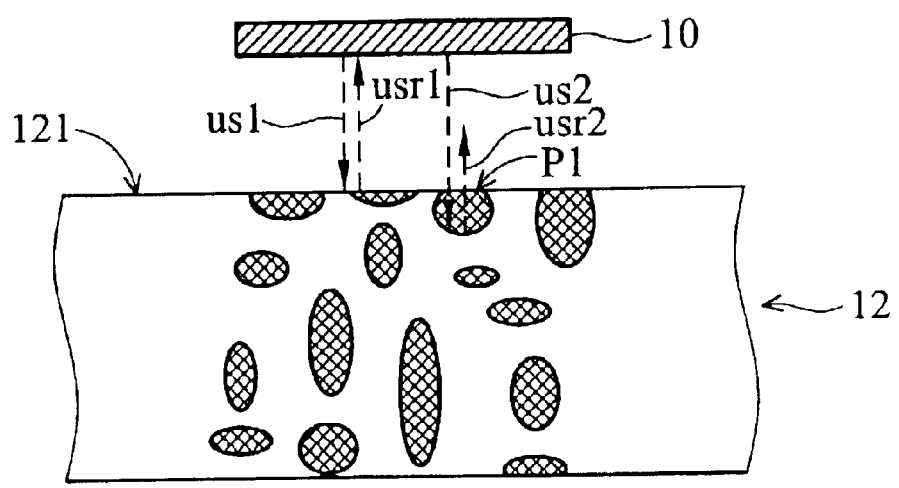
FIG. 3b is another diagram of the measuring method according to the present invention.

The present invention illustrates the relationship between the time delay in the reflected signals usf1~usfn to the pore depth of pores p1. Please refer to FIG. 3b. Briefly, two groups of ultrasound transmitters and receivers are employed to illustrate this relationship. It is to be understood that the invention is not limited to the disclosed embodiments. For example, the ultrasound sensing device 10 can send out two ultrasound signals us1 and us2. When the ultrasound signal us1 reaches the surface 121 of the polishing pad, a signal usr1 is reflected from the surface 121 to the ultrasound receiver of the sensing device 10 after time t1. In addition, when the ultrasound signal us2 reaches the bottom of pore p1 on the polishing pad, a signal usr2 is reflected from the bottom of pore p1 to another ultrasound receiver of the sensing device 10 after time t2. Because the time t2 is not equal to time t1, a pore depth of the pore p1 on the surface 121 is obtained according to the difference and speed of the ultrasound. Thus, the processor unit 14 can obtain depths of pores p1 on the surface 121 and establish first depth difference data according to the time delay in the reflected signals.

In step 18, the polishing pad 12 is rotated by the rotating platen 13 of the polishing machine and steps 10~16 are repeatedly executed to establish second to Nth depth difference data, thereby obtaining the pore depth on the entire surface 121 of polishing pad 12.

In step 20, the process unit 14 calculates the size of the pores pi on the polishing pad 12 according to the first to Nth depth difference data. Typically, the diameter of pores on the surface of the polishing pad is between 20~120 $\mu$m.

In step 22, the first to Nth depth difference data is converted to a relational image 18 relative to the surface 121 and the pores p1 of the polishing pad 12.

In addition, the process unit 14 calculates the relationship between the size of the pores and the surface of the polishing pad according to the first to Nth depth difference data. Alternately, the process unit 14 calculates the pore size per surface area of the polishing pad according to the size of the pores and the surface 121 of the polishing pad 12.

Thus, the present invention can obtain the depth and size of the pores on the surface of the polishing pad, as well as, the pore size per surface area of the polishing pad. Consequently, process engineers can adjust process parameters and control the polishing rate to improve throughput according to the measured data.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of measuring pore depth on the surface of a polishing pad during processing, wherein the polishing pad is disposed on a rotation plate of a polishing machine, the method comprising:
   providing a planar ultrasound sensing device disposed a predetermined distance above the surface of the polishing pad;
   sending out a plurality of ultrasound signals to the surface of the polishing pad and pores therein;
   receiving a plurality of reflected signals from the pad surface and constituent pores;
   determining the difference between pore depth and the surface to establish first depth difference data according to the time delay in the reflected signals;
   rotating the polishing pad and sending, receiving and determining the difference between pore depth and the surface to establish second to Nth depth difference data;
   computing the size of the pores on the polishing pad according to the first to Nth depth difference data; and
   converting the first to Nth depth difference data into a relational image relative to the surface and the pores of the polishing pad.

2. The method as claimed in claim 1, further comprising a step of displaying the relation image relative the surface and the pores of the polishing pad on a display device.

3. The method as claimed in claim 1, further comprising a step of computing a relationship between size and depth of the pores on the polishing pad according to the first to Nth depth difference data.

4. The method as claimed in claim 3, further comprising a step of computing pore size per surface unit of the polishing pad according to the size of pores and the surface area of the polishing pad.

5. The method as claimed in claim 4, wherein the ultrasound signals are sent out by ultrasound transmitters in the planar ultrasound sensing device, and the reflected signals are received by ultrasound receivers in the planar ultrasound sensing device.

6. The method as claimed in claim 5, wherein the operational frequency of the ultrasound transmitters is between 0.1 to 5 GHz.

* * * * *